(12) United States Patent
Schneider et al.

(10) Patent No.: US 8,093,439 B2
(45) Date of Patent: Jan. 10, 2012

(54) METHOD FOR OLIGOMERIZATION AND/OR POLYMERIZATION OF ETHYLENE WITH FLUSHING OF EQUIPMENT AND PIPING

(75) Inventors: Richard Schneider, Uffing (DE); Peter M. Fritz, Unterhaching (DE); Sebastian Muschelknautz, Munich (DE); Heinz Bölt, Wolfratshausen (DE); Talal Ali, Riyadh (SA); Fuad Mosa, Riyadh (SA)

(73) Assignees: Saudi Basic Industries Corporation, Riyadh (SA); Linde AG, Munich (DE)

( * ) Notice: Subject to any disclaimer, the term of this patent is extended or adjusted under 35 U.S.C. 154(b) by 105 days.

(21) Appl. No.: 12/083,807

(22) PCT Filed: Sep. 26, 2006

(86) PCT No.: PCT/EP2006/009321
§ 371 (c)(1),
(2), (4) Date: Aug. 24, 2009

(87) PCT Pub. No.: WO2007/045328
PCT Pub. Date: Apr. 26, 2007

(65) Prior Publication Data
US 2009/0318639 A1  Dec. 24, 2009

(30) Foreign Application Priority Data
Oct. 19, 2005  (EP) ..................................... 05022778

(51) Int. Cl.
*C07C 2/02* (2006.01)
*C08F 6/00* (2006.01)

(52) U.S. Cl. ..................... 585/520; 585/502; 528/502 D

(58) Field of Classification Search ................... 528/502, 528/520; 585/502, 520
See application file for complete search history.

(56) References Cited

U.S. PATENT DOCUMENTS 3,816,383 A * 6/1974 Stotko .............................. 526/67
5,523,508 A * 6/1996 Krawczyk et al. ............. 585/523

FOREIGN PATENT DOCUMENTS

DE  4338414 C1 *  3/1995
DE  4338415 C1 *  3/1995

OTHER PUBLICATIONS

Translation of DE 4338414 C1.*

* cited by examiner

*Primary Examiner* — David W Wu
*Assistant Examiner* — Elizabeth Eng
(74) *Attorney, Agent, or Firm* — Kramer Levin Naftalis & Frankel LLP

(57) ABSTRACT

The present invention relates to a method for oligomerization or polymerization of ethylene and/or alpha-olefins utilizing reactor equipment and other equipment wherein starting material comprising monomer(s), catalyst, cocatalyst and solvent is transferred to the reactor equipment via first piping, and product material comprising oligomer and/or polymer, non-reacted monomer(s), catalyst, cocatalyst and solvent is discharged from the reactor equipment via second piping, characterized in that the first piping, second piping, reactor equipment and/or other equipment are flushed with a product fraction obtained by said or a respective previous method prior to and/or after that oligomerization or polymerization method.

8 Claims, 1 Drawing Sheet

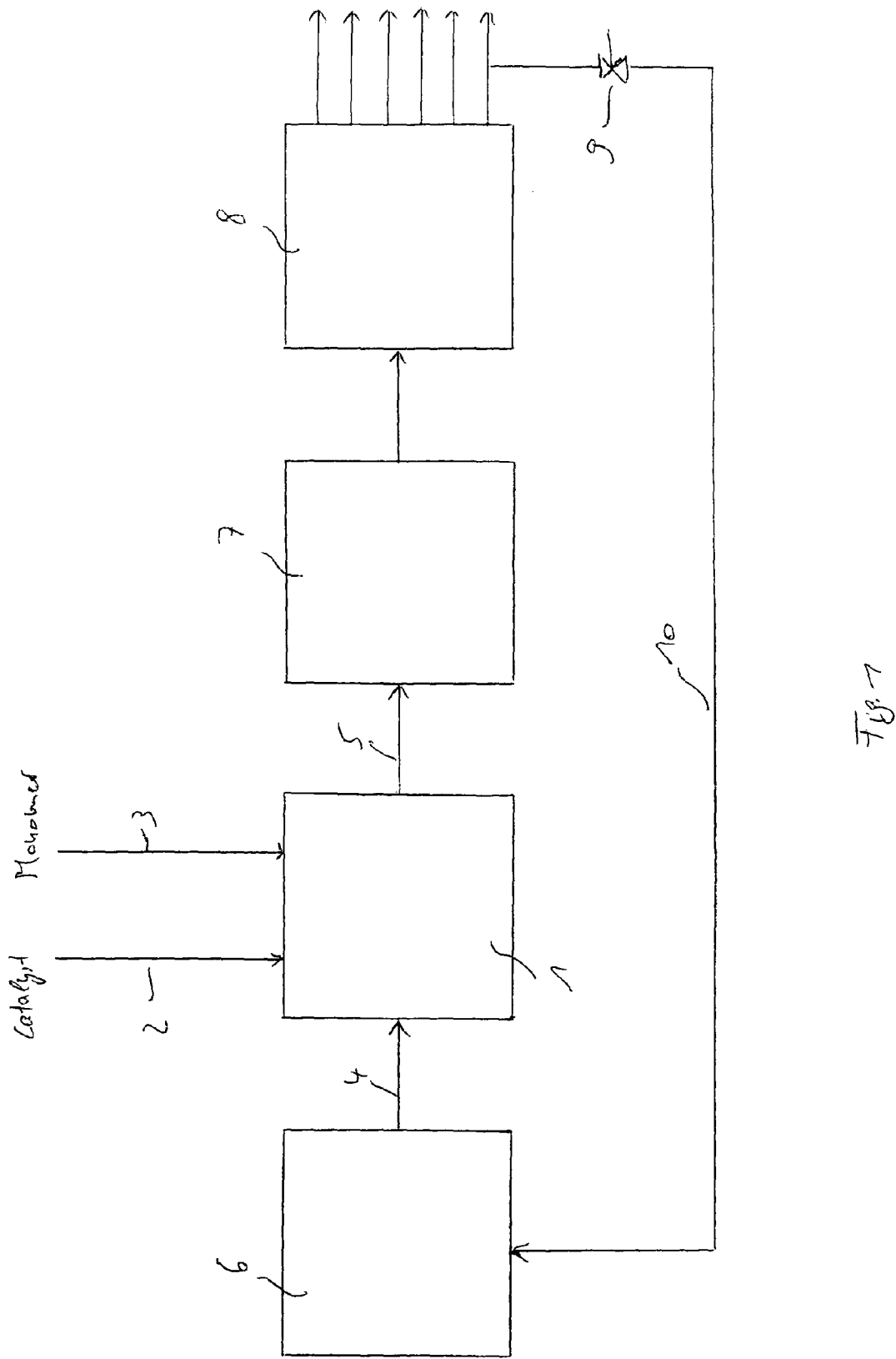

METHOD FOR OLIGOMERIZATION AND/OR POLYMERIZATION OF ETHYLENE WITH FLUSHING OF EQUIPMENT AND PIPING

The present invention relates to a method for, oligomerization or polymerization of ethylene and/or alpha-olefins utilizing reactor equipment and other equipment wherein starting material comprising monomer(s), catalyst, cocatalyst and solvent is transferred to a reactor equipment via first piping, and product material comprising oligomer and/or polymer, non-reacted monomer(s), catalyst, cocatalyst and solvent is discharged from the reactor equipment via second piping.

Methods for oligomerization or polymerization of ethylene and other alpha-olefins are widely known in the art. For example, DE 43 38 414 C1 discloses a process for the preparation of linear alpha-olefins by oligomerization of ethylene, wherein oligomerization takes place in the presence of an organic solvent and a homogenous liquid catalyst. Usually, a catalyst is utilized in that process comprising a zirconium component and an organoaluminum component which acts as a cocatalyst.

Such oligomerization or polymerization methods are usually carried out in that starting material comprising monomer(s), catalyst, cocatalyst and solvent is transferred to a reactor equipment via first piping. After conversion in the reactor equipment, product material comprising oligomer and/or polymer, non-reacted monomer(s), catalyst, cocatalyst and solvent may be discharged from the reactor equipment and can be further processed. For example, in the product material the catalyst may be deactivated, the solvent may be separated and the oligomer and/or polymer may be fractionated.

Usually, such methods are continuously operated wherein non-reacted monomer(s) and solvent may be circulated in the oligomerization or polymerization plant.

From time to time, the oligomerization or polymerization plant has to be cleaned as fouling, or in the worst case plugging may occur, especially fouling at the reactor walls and the walls of the piping. This cleaning is usually achieved by flushing the pipings and the reactor equipment with a, preferably, hot flushing medium. This flushing medium may be any suitable solvent, preferably white oil can be used, which has, generally, to be imported into the plant.

The flushing of piping and reactor equipment results in significant quantities of contaminated flushing media which are to be disposed in a difficult and cost-intensive manner.

Additionally, flushing of piping and equipment is especially relevant for that plant sections containing reactive organoaluminum components, such as aluminum alkyls, which act as a cocatalyst or activator. Thus, it is important to remove the organoaluminum components completely before the reactor equipment or piping is opened and exposed to atmosphere.

It is an object of the present invention to provide a method for oligomerization or polymerization which overcomes the drawbacks of the prior art. Especially a method shall be provided which avoids the use of a flushing medium which is to be disposed in a difficult and cost-intensive manner, but which flushing medium is suitable to remove reactive reaction components prior to maintenance.

This object is achieved in that the first piping, second piping, reactor equipment and/or other equipment are flushed with a product fraction obtained by separating the reaction product into relatively lighter and heavier molecular weight fractions by distillation or other conventional means. The product fraction used to flush the reactor equipment and/or other equipment can be obtained by continuous separation of the reactor product and storing the selected product fraction for latter use. Alternatively the selected product fraction can be obtained by subjecting a quantity of the reactor product to batch separation to produce the desired molecular weight fraction of product. In either case the product fraction can be used immediately or stored for future use. Accordingly, the selected molecular weight product fraction can be obtained by said or a respective previous method prior to and/or after that oligomerization or polymerization method. Of course, it is understood by someone skilled in the art that flushing the plant before carrying out the method for oligomerization or polymerization utilizes a product fraction obtained in a respective previous method. The flushing method of the present invention can be employed in a reactor system for the oligomerization or polymerization of ethylene and/or alpha-olefins which comprises all or a portion of a reactor, storage vessels, lines, quenching units, separation units, and catalyst removal units.

Most preferably, the method is the oligomerization of ethylene.

In one embodiment, the product fraction is obtained from the product material by further processing, preferably purification and/or separation.

It is still preferred that the product fraction is a fraction of linear alpha-olefins (LAO).

Further, the LAO fraction may be a heavier product fraction, preferably the fraction containing $C_{12}$-$C_{18}$ product.

It is also preferred that flushing is carried out for piping and equipment containing organoaluminum compounds.

Even preferred, the product fraction utilized for flushing is (re)processed in the method.

Finally, one embodiment is characterized in that (re)processing comprises processing in a catalyst deactivation section, solvent removal and product separation section and/or discharge section.

Surprisingly, it was found that a specific product fraction obtained in the method for oligomerization or polymerization can be suitably utilized as a flushing medium. Thus, no additional flushing medium is required or is to be imported. The respective product fraction, preferably a specific LAO-fraction in a method for oligomerization of ethylene containing $C_{12}$-$C_{18}$ product, may be obtained within that method at a section before or after catalyst deactivation section, solvent removal and separation section and/or discharge section. The disposal of the flushing medium may thus be easily achieved within the oligomerization or polymerization plant in that the "contaminated" flushing medium is (re)processed in any of the plant sections following the reactor. Thus, no cost-intensive disposal of the flushing medium or its export is necessary.

The inventive method is preferably suitable for flushing piping and equipment containing organoaluminum components, such as aluminum alkyls, which are utilized in the oligomerization or polymerization method as cocatalyst. These reactive cocatalysts may thus be easily removed completely before the system is opened and exposed to atmosphere for maintenance.

Additional features and advantages of the inventive method are further illustrated with reference to the accompanying drawing, wherein the FIGURE illustrates a schematic diagram of a plant for the production of linear alpha-olefins.

FIG. 1 illustrates a reactor equipment 1 forming the basis reactor for oligomerization of ethylene to form linear alpha-olefins. Various piping 2, 3, 4, 5 is connected to that reactor equipment 1 for delivering monomer(s), catalyst and cocatalyst to the reactor and for removing reaction product from that reactor equipment 1. Additional piping (not shown) may be provided, e.g. for delivering solvent. As cocatalyst preferably an organoaluminum component is utilized which may be stored prior to introduction into the reactor equipment 1 in a cocatalyst containing vessel 6. After oligomerization in the reactor equipment 1 the reaction product, non-reacted monomer(s), catalyst, cocatalyst and solvent may be discharged and may be transferred to a catalyst removal section 7 and afterwards to a product separation section 8 where the product may be separated into individual fractions. One product fraction, preferably a heavier product fraction of the oligomerization, such as the fraction containing $C_{12}$-$C_{18}$ product, may be, at least partially, transferred back as a flushing medium into the organoaluminum component containing vessel (or any other equipment or piping containing cocatalyst or any other reactive component) for flushing the respective sections. A valve 9 is located in flushing line 10 so that flushing medium may be introduced into the cocatalyst vessel as desired. Thus, it is possible to flush selected parts of the equipment and piping prior to maintenance and exposition and opening of that sections to atmosphere. Additionally, no imported flushing medium is necessary for this purpose.

The features disclosed in the foregoing description, in the claims and in the drawing may, both separately and in any combination thereof, be material for realizing the invention in diverse forms thereof.

The invention claimed is:

1. A method for flushing a reactor system after it is used to perform an oligomerization or polymerization reaction of ethylene and/or alpha-olefins wherein the reactor system feed comprised at least one monomer, a catalyst, a cocatalyst and a solvent, and the reactor system product comprised oligomers and/or polymers having a range of molecular weights, catalyst, cocatalyst and solvent, characterized in that at least a portion of the reactor system product is continuously or by batch separated into at least two molecular weight fractions of oligomer and/or polymer product and after the performance of said reaction in the reactor system, the reactor system is flushed by contacting it with at least one of said molecular weight fractions of oligomer and/or polymer product.

2. The method according to claim 1, wherein the reactor system is used for the oligomerization of ethylene.

3. The method according to claim 2, wherein the molecular weight fraction of oligomer and/or polymer product used to flush the reaction system is purified by catalyst deactivation.

4. The method according to claim 2, wherein the product molecular weight fraction used to flush the reactor system comprises linear alpha-olefins (LAO).

5. The method according to claim 4, wherein the LAO product fraction is a $C_{12}$-$C_{18}$ product fraction.

6. The method according to claim 1, wherein flushing is carried out for piping and equipment of the reactor system containing organoaluminum compounds.

7. The method according to claim 1, wherein the product fraction utilized for flushing is (re)processed after the flushing operation.

8. The method according to claim 7, characterized in that (re)processing comprises catalyst deactivation, solvent removal and product separation.

* * * * *